(12) United States Patent
Scheurer et al.

(10) Patent No.: US 8,636,697 B2
(45) Date of Patent: Jan. 28, 2014

(54) INSERTION HEAD FOR MEDICAL OR PHARMACEUTICAL APPLICATIONS

(75) Inventors: Simon Scheurer, Bern (CH); Marcel Hunn, Langenthal (CH); Jürg Liniger, Ostermundigen (CH)

(73) Assignee: Roche Diagnostics International AG, Rotkrouz (CH)

( * ) Notice: Subject to any disclaimer, the term of this patent is extended or adjusted under 35 U.S.C. 154(b) by 339 days.

(21) Appl. No.: 11/673,939

(22) Filed: Feb. 12, 2007

(65) Prior Publication Data

US 2007/0129688 A1 Jun. 7, 2007

Related U.S. Application Data

(63) Continuation of application No. PCT/CH2005/000459, filed on Aug. 4, 2005.

(30) Foreign Application Priority Data

Aug. 13, 2004 (DE) .......................... 10 2004 039 408

(51) Int. Cl.
*A61M 5/32* (2006.01)
*A61M 5/00* (2006.01)

(52) U.S. Cl.
USPC .......................................... 604/174; 604/263

(58) Field of Classification Search
USPC ......... 604/263, 104–110, 177, 198, 174, 158, 604/164.08, 93.01
See application file for complete search history.

(56) References Cited

U.S. PATENT DOCUMENTS

| | | | | |
|---|---|---|---|---|
| 4,306,563 A | * | 12/1981 | Iwatschenko | 604/265 |
| 4,631,058 A | * | 12/1986 | Raines | 604/263 |
| 4,755,173 A | * | 7/1988 | Konopka et al. | 604/167.02 |
| 4,835,248 A | * | 5/1989 | Bader et al. | 528/328 |
| 4,863,432 A | * | 9/1989 | Kvalo | 604/177 |
| 4,927,603 A | * | 5/1990 | Fischer et al. | 422/67 |
| 5,176,662 A | * | 1/1993 | Bartholomew et al. | 604/513 |
| 5,522,803 A | * | 6/1996 | Teissen-Simony | 604/177 |
| 5,545,143 A | * | 8/1996 | Fischell | 604/180 |
| 5,584,813 A | * | 12/1996 | Livingston et al. | 604/177 |
| 5,814,020 A | | 9/1998 | Gross | |
| 5,858,001 A | | 1/1999 | Tsals et al. | |
| 5,951,522 A | * | 9/1999 | Rosato et al. | 604/177 |
| 5,957,895 A | | 9/1999 | Sage et al. | |

(Continued)

FOREIGN PATENT DOCUMENTS

DE 19821723 A1 11/1999
DE 101 17 286 10/2002

(Continued)

OTHER PUBLICATIONS

EPO Machine Translation FR 2752164.pdf.*

*Primary Examiner* — Bhisma Mehta
*Assistant Examiner* — Bradley Osinski
(74) *Attorney, Agent, or Firm* — Dinsmore & Shohl, LLP (57) ABSTRACT

An insertion head for medical or pharmaceutical uses including a housing with a side that can be positioned on tissue and a penetrating device with a tip, the penetrating device carried by the housing in a protected orientation in which the housing covers the tip and a penetrating orientation in which the tip protrudes, wherein the penetrating orientation is angled relative to the protected orientation.

31 Claims, 6 Drawing Sheets

(56) References Cited

U.S. PATENT DOCUMENTS

| | | | |
|---|---|---|---|
| 5,968,011 A * | 10/1999 | Larsen et al. | 604/288.02 |
| 5,980,506 A * | 11/1999 | Mathiasen | 604/535 |
| 5,997,504 A * | 12/1999 | Bell | 604/164.01 |
| 6,017,328 A * | 1/2000 | Fischell et al. | 604/180 |
| 6,056,718 A * | 5/2000 | Funderburk et al. | 604/93.01 |
| 6,090,068 A * | 7/2000 | Chanut | 604/93.01 |
| 6,261,259 B1 | 7/2001 | Bell | |
| 6,302,866 B1 * | 10/2001 | Marggi | 604/174 |
| 6,355,021 B1 * | 3/2002 | Nielsen et al. | 604/263 |
| 6,379,335 B1 * | 4/2002 | Rigon et al. | 604/177 |
| 6,419,699 B1 * | 7/2002 | Schuessler | 623/11.11 |
| 6,500,150 B1 | 12/2002 | Gross et al. | |
| 6,520,938 B1 * | 2/2003 | Funderburk et al. | 604/164.08 |
| 6,537,255 B1 * | 3/2003 | Raines | 604/177 |
| 6,579,267 B2 * | 6/2003 | Lynch et al. | 604/174 |
| 6,676,633 B2 * | 1/2004 | Smith et al. | 604/110 |
| 6,749,588 B1 * | 6/2004 | Howell et al. | 604/164.08 |
| 6,749,589 B1 * | 6/2004 | Douglas et al. | 604/165.01 |
| 6,755,805 B1 * | 6/2004 | Reid | 604/110 |
| 6,824,530 B2 * | 11/2004 | Wagner et al. | 604/162 |
| 6,840,922 B2 * | 1/2005 | Nielsen et al. | 604/263 |
| 6,878,134 B2 * | 4/2005 | Rogers et al. | 604/164.01 |
| 6,887,270 B2 * | 5/2005 | Miller et al. | 623/11.11 |
| 6,911,020 B2 * | 6/2005 | Raines | 604/177 |
| 6,921,388 B2 * | 7/2005 | Swenson | 604/177 |
| 6,923,791 B2 * | 8/2005 | Douglas | 604/167.05 |
| 6,949,084 B2 * | 9/2005 | Marggi et al. | 604/174 |
| 6,969,372 B1 * | 11/2005 | Halseth | 604/164.08 |
| 6,997,902 B2 * | 2/2006 | Thorne et al. | 604/110 |
| D526,409 S * | 8/2006 | Nielsen et al. | D24/108 |
| 7,097,637 B2 * | 8/2006 | Triplett et al. | 604/192 |
| 7,147,623 B2 * | 12/2006 | Mathiasen | 604/164.08 |
| 7,214,207 B2 * | 5/2007 | Lynch et al. | 604/93.01 |
| 2002/0045867 A1 * | 4/2002 | Nielsen et al. | 604/263 |
| 2002/0123724 A1 * | 9/2002 | Douglas et al. | 604/177 |
| 2002/0193744 A1 * | 12/2002 | Alesi et al. | 604/192 |
| 2003/0069546 A1 * | 4/2003 | Sandstrom et al. | 604/263 |
| 2003/0083624 A1 * | 5/2003 | Smith et al. | 604/177 |
| 2003/0105449 A1 * | 6/2003 | Raines | 604/506 |
| 2003/0181874 A1 * | 9/2003 | Bressler et al. | 604/263 |
| 2004/0044306 A1 * | 3/2004 | Lynch et al. | 604/93.01 |
| 2004/0158207 A1 | 8/2004 | Hunn et al. | |
| 2004/0158230 A1 | 8/2004 | Hunn et al. | |
| 2004/0215154 A1 * | 10/2004 | Hwang et al. | 604/263 |
| 2005/0283125 A1 | 12/2005 | Barkhahn et al. | |
| 2006/0015063 A1 * | 1/2006 | Butikofer et al. | 604/93.01 |
| 2006/0030824 A1 | 2/2006 | Hunn et al. | |
| 2006/0173414 A1 * | 8/2006 | Buetikofer et al. | 604/164.01 |
| 2006/0183985 A1 * | 8/2006 | Brister et al. | 600/316 |
| 2006/0229573 A1 * | 10/2006 | Lamborne | 604/263 |
| 2007/0016149 A1 | 1/2007 | Hunn et al. | |
| 2007/0129688 A1 * | 6/2007 | Scheurer et al. | 604/263 |

FOREIGN PATENT DOCUMENTS

| | | |
|---|---|---|
| DE | 10 2004 002 472 | 8/2005 |
| FR | 2752164 | 2/1998 |
| FR | 2752164 A1 * | 2/1998 |
| JP | 7-510 A | 1/1995 |
| JP | 10-503963 A | 4/1998 |
| WO | 02/081012 | 10/2002 |
| WO | 2004/029457 | 4/2004 |
| WO | 2004/064583 | 8/2004 |
| WO | 2004/064898 | 8/2004 |
| WO | 2004/098682 | 11/2004 |

* cited by examiner

INSERTION HEAD FOR MEDICAL OR PHARMACEUTICAL APPLICATIONS

CROSS-REFERENCE TO RELATED APPLICATION(S)

This application is a continuation of International Application No. PCT/CH2005/000459, filed on Aug. 4, 2005, which claims priority to German Application No. 10 2004 039 408.3, filed on Aug. 13, 2004, the contents of both of which are incorporated in their entirety herein by reference.

BACKGROUND

The present invention relates to devices for dispensing, delivery, infusing or administering substances, and to methods of making and using such devices. More particularly, it relates to an insertion head for medical or pharmaceutical applications or uses which may be positioned on organic tissue, e.g. human skin, and comprises a puncturing device which penetrates the tissue when or after the insertion head has been positioned on the tissue. The insertion head may, in particular, be a component of an infusion set for administration of a medicament.

Such an insertion head is known from DE 198 21 723 C1. The insertion head comprises a housing, a flexible cannula which projects or extends from an underside of the housing and a puncturing needle which serves for positioning the flexible cannula subcutaneously in the tissue of a patient. For inserting into the tissue, the puncturing needle projects through the cannula and the cannula closely surrounds the puncturing needle. To protect a user of the insertion head from puncturing injuries, a needle protector is releasably fastened to the housing, extending or projecting from the housing and enclosing the cannula and the puncturing needle. The puncturing needle projecting from the underside of the insertion head with the surrounding cannula and, in particular, also the needle protector considerably increase the volume of the insertion head and thereby also the packaging thereof.

SUMMARY

One object of the present invention is to reduce the packaging volume for an insertion head which comprises a puncturing device and a protective device for the puncturing device.

In one embodiment, the present invention relates to an insertion head for medical or pharmaceutical applications or uses which comprises a housing with an underside which may be positioned on organic tissue and a puncturing device. The puncturing device comprises a puncturing section with a tip for penetrating, piercing or pricking the tissue. In some embodiments, the puncturing section projects from the underside of the housing. In principle, however, it may instead project from a side of the housing, provided that it projects sufficiently far beyond the underside for penetrating the tissue. The puncturing section may project beyond or extend from the underside of the housing, directly from the underside, by a length adapted to subcutaneous applications or uses. For applications or uses inside the skin or in intramuscular tissue, the puncturing section may be correspondingly shorter or longer. The puncturing section is understood to be the longitudinal section of the puncturing device which, during application, projects or extends into the tissue.

In one embodiment, the present invention comprises an insertion head for medical or pharmaceutical uses comprising a housing with a side that can be positioned on tissue and a penetrating device with a tip, the penetrating device carried by the housing and moveable from a protected orientation in which the housing covers the tip to a penetrating orientation in which the tip protrudes, wherein the penetrating orientation is angled relative to the protected orientation.

An insertion head for medical or pharmaceutical applications or uses including a housing with a bottom side that can be positioned on organic tissue and a pricking device with a pricking section with a tip while being retained by the housing in a protected position in which the housing covers the tip as well as in pricking position in which the tip protrudes from the bottom side, wherein in the pricking position, the pricking section is in a tilted position relative to the protected position.

In some embodiments, the insertion head is a component of an infusion set for administering insulin, a pain killer or another medicament which may be administered by infusion. The insertion head may also be used for diagnostic purposes instead of for an administration of medicaments or, in principle, of a different product which can be administered. In such applications, the puncturing section may serve as a carrier for a sensor for measuring, for example, the concentration of glucose in a body fluid or a different physical and/or biochemical variable which is crucial or may be crucial for the state of health of a patient. The insertion head may, for diagnostic purposes, be formed as a perfusion device. In such an embodiment, a rinsing fluid flows through the puncturing section after insertion into the tissue, which rinsing fluid absorbs one or more specific constituents of the body fluid when flowing to analyze the rinsing fluid enriched with the relevant constituent or the plurality of constituents.

In some embodiments, the insertion head may form a combined device for the administration of a product and a diagnostic device. The puncturing section can be formed for the delivery of a product, which may be, in particular, a medicament or a rinsing fluid, or for the removal of a body fluid or only one or a plurality of specific constituents of a body fluid. In such embodiments the puncturing section forms at least one cross section of flow. The puncturing section may also serve for the delivery and removal of substances in combination. If the insertion head is formed as a measuring device, the puncturing section may also only serve for positioning of a sensor or a part of a sensor, i.e. purely as mechanical insertion device. In a development as a measuring device, it may also serve, in addition to the mechanical inserting, for the transmission of control signals to the sensor and/or of measuring signals from the sensor. In combined embodiments and uses it may possess at least one cross section of flow for the transport of substances, i.e. a flow line, and at least one signal line. In some embodiments, the signal line may be dispensed with if the sensor is designed for the wireless reception of control signals and/or the wireless dispatching of measuring signals.

In some embodiments, the puncturing device may also comprise two or more puncturing sections, which project separately. Thus, a first puncturing section may serve for the transportation of substances into the tissue and a further, second puncturing section may serve for the transportation of substances out of the tissue and/or for inserting a sensor or a part of a sensor. With a plurality of puncturing sections, which each comprise a flow section, various substances may be administered with the same insertion head. This may also be realized by means of a puncturing section which forms a plurality of separate cross-sections of flow.

In some embodiments, to protect the user from puncturing injuries, a protective device is provided, which covers at least the tip of the puncturing section or the entire puncturing section in a first state of the insertion head. In a second state, into which the insertion head may be brought for use, the tip of the puncturing section is exposed and may be inserted into the tissue.

According to some embodiments of the present invention, the housing itself forms the protective device, i.e. the insertion head is provided with an integrated protective device. The puncturing device may adopt at least two predetermined positions relative to the housing, namely a first position in a first state of the insertion head and a second position in a second state of the insertion head. In both positions, the puncturing device is held by the housing, i.e. in both positions it is sufficiently fixedly connected to the housing to form a unit with the housing with regard to handling. The first position of the puncturing device may be referred to hereinafter as the protected position and the second position as the puncturing position.

In some embodiments, in the protected position, the puncturing section adopts a tilted position relative to the puncturing position, so that the housing covers the tip of the puncturing section.

In some preferred embodiments, the puncturing device is permanently connected to the housing in a movable manner. The fact that the puncturing device is permanently connected to the housing means that at least for the movement from the protected position into the puncturing position and/or from the puncturing position into the protected position it is not released from the housing. In such embodiments, the puncturing device is permanently connected to the housing in the sense that it may not be released at all from the housing, at least not without the exertion of an outstanding force or by destruction.

In some preferred embodiments of the present invention, the puncturing device is connected to the housing in such a manner that the puncturing section may be pivoted relative to the housing. Advantageously, the puncturing section may be pivoted into the housing so that at least the tip thereof or the entire puncturing section is set back behind the housing, in some embodiments behind or within the underside thereof, and as a result is covered by the housing. In principle, however, it is also conceivable as an alternative that the puncturing section has a flexural elasticity which is sufficiently high to bend the puncturing section with the tip thereof towards the housing, so that the tip projects into a receptacle of the housing and is releasably caught therewith in the housing, or otherwise is releasably held in this bending state counter to the restoring elasticity thereof. Such an embodiment is, in particular, conceivable when the puncturing section in the puncturing position encloses an acute angle with the underside of the housing. It is also conceivable that, for such a bending, the puncturing section is fastened to the housing a small distance behind the underside of the housing to thereby obtain a certain bending length already inside the housing. It is advantageous, on the other hand, if the puncturing section in the puncturing position projects directly from the underside in contact with the tissue surface during use, i.e. is clamped or connected to the underside in such a manner, fixedly or optionally axially movably and otherwise fixedly, that when penetrating a tissue, the flexible length of the insertion section is as short as possible. This applies, in particular, when the puncturing section, as in some preferred embodiments, comprises a thin needle. A puncturing section projecting directly from the underside is, in any case, preferred when the puncturing section does not have to be distorted for the protected position. In still a further alternative, the housing may form a displacement guide for the puncturing device, on which the puncturing device is guided in a translatory manner during its movement from the protected position into the puncturing position and/or from the puncturing position into the protected position. In some embodiments, the puncturing device is releasably fastened in a first connection to the housing in the protected position and also releasably fastened in a further, second connection in the puncturing position, wherein when the respective connection for the transfer into the respective other position is released, the puncturing device is separated from the housing and subsequently the new connection is established. In some embodiments, the two connections may, in particular, be a respective plug connection and/or catching connection.

In a preferred embodiment in which the puncturing section may be pivoted relative to the housing, the puncturing device and the housing form with one another an articulation with an axis of articulation pointing and/or extending transversely to the puncturing section. The puncturing device may be rotated about the axis of articulation relative to the housing. For the formation of such an articulation, the housing or the puncturing device may form a bearing or bushing and the other component may form the bearing pin. The bearing has to enclose the bearing pin over an angle of more than 180° when the puncturing device is to be fixedly held by the housing.

In principle, in some embodiments, it is sufficient for the puncturing device to be movable relative to the housing in only one direction and/or only so moved once, from the protected position into the puncturing position. However, in some embodiments, the puncturing device is optionally movable to and from between two positions, so that the puncturing device may be moved into the puncturing position for use and again into the protected position for disposal. In some embodiments, the connection between the puncturing device and the housing is, or comprises, a positive connection, which may form an articulation. The connection may alternatively, however, also be non-positive or even produced by material bond, for example when the puncturing section is bent into the protected position.

In some embodiments, the puncturing device is sufficiently fixedly held in at least two different positions. This means that, during puncturing, a user does not have to hold the puncturing section, but rather the housing or an insertion aid guiding the housing during puncturing, so that the puncturing section automatically penetrates the tissue when the housing is positioned on the tissue. The puncturing device is also held in the protected position, so that even at light vibrations it does not leave the protected position. In some preferred embodiments, the puncturing device catches with the housing in predetermined positions. The catching connection is releasable in the protected position. The catching connection may be releasable or unreleasable in the puncturing position. The catching connection may be formed by a connecting articulation itself, for example by the aforementioned bearing pin and bushing thereof having polygonal cross-sections adapted to one another. The catching elements may instead or additionally, however, also be provided outside the respective articulated connection.

In a preferred development of the present invention, the puncturing device is connected to the housing such that it is able to adopt two or more predetermined puncturing positions, each of the puncturing positions being predetermined as catching positions. Thus, the puncturing section may project in one of the puncturing positions perpendicularly beyond the underside of the housing, i.e. at a right angle, and in a further puncturing position may enclose an angle of less than 90°, preferably an angle of less than 45°, with the underside. The user may freely choose between the predetermined puncturing positions. If the different positions of the puncturing device or only the different puncturing positions are predetermined to be non-positive, so that the puncturing device is held non-positively on the housing in the relevant positions, the puncturing section may be moved relative to the underside of the housing into any angular position between 0 and 90°, in some embodiments, into any suitable angular position between 0 and 180°.

In some embodiments, for the connection to the housing, the puncturing device comprises a connecting structure from which the puncturing section projects. In some preferred embodiments, in the puncturing position the connecting structure forms part of or the entire underside of the insertion head, and rests with the underside thereof or part of the underside thereof, from which the puncturing section projects, on a tissue when the puncturing section is completely inserted into the tissue. In principle, however, the underside of the connecting structure may also be set back a small distance behind the contact surface of the insertion head.

In some embodiments, the housing forms an integrated protective device in the form of a receptacle which is open toward one outer side of the housing, so that the puncturing section may be pivoted into this receptacle or at least be bent with the tip thereof into the receptacle. It is also conceivable, in principle, that the puncturing device, in a first state of the insertion head, is received in the receptacle or at least with the tip thereof is received in the receptacle, and is releasably fastened to the housing in the protected position. The penetrating structure, or the tip, may be releasably held in the protected position by a catching connection, and in the puncturing position can be connected again to the housing, preferably by a catching connection. In some embodiments, the receptacle is formed on the underside of the housing. It is further advantageous, particularly for a moveable or pivoting puncturing section, if the receptacle is not only open towards the respective outer side, e.g. the underside, but also to an articulated connection of the puncturing device. The receptacle may also be open toward the underside and towards another outer side, for example to allow pivoting movements about different pivoting axes.

In some embodiments, the puncturing section may, in particular, comprise a flexible element, for example in the form of a flexible cannula, and a stabilizing element, and it may be formed solely from these parts. The stabilizing element in such embodiments serves for stabilizing the flexible element during puncturing and may, after the insertion thereof into the tissue, be advantageously removed to cause as little irritation as possible in the tissue during use. In some preferred embodiments, the stabilizing element forms a puncturing edge of the puncturing section.

In some embodiments, a puncturing needle, e.g. a steel needle, which remains in the tissue during the application, may also form the puncturing section. In preferred subcutaneous applications, such a puncturing section should be as short as possible, in some preferred embodiments, at most 12 mm or at most 8 mm. The needle should, on the one hand, be as flexible as possible for remaining in the tissue, i.e. elastically flexible but, on the other hand, has to be sufficiently rigid that it is able to penetrate into and/or through the human skin.

In further preferred embodiments, the rigidity of the puncturing section is automatically reduced when the puncturing section is inserted into the tissue. Thus the puncturing section, for example, may be made from a material which, in the range of body temperature, for example when exceeding a temperature of 35 or 36° C., or thereunder, namely in the region of 32° to 34° C., is markedly more flexible than at lower temperatures. Thus, the puncturing section may be formed as described in PCT/EP 04/00310, PCT/EP 04/00309, DE 101 17 286 A or DE 10 2004 002 472, which are incorporated herein by reference.

In some embodiments, the puncturing section may be formed completely or at least partially from a polymer material which, upon contact with body fluid, becomes softer and, as a result, the puncturing section becomes more flexible. In some embodiments, the softening may be brought about by an absorption of water and thus on a loosening of secondary bonds of the polymer material associated therewith. In principle, the polymer material may, however, be also partially dissolved and the flexibility thereby increased. The use of a polymer material which can be softened by absorption, which in addition softens in the aforementioned temperature range due to the effect of the temperature, may also be advantageous. In such embodiments, an additional stabilizing element may be dispensed with and the puncturing section is nevertheless more flexible in the tissue than a conventional puncturing needle.

In some embodiments of the present invention, the insertion head may be a component of an infusion set and/or diagnostic set, which also comprises a supply line and/or discharge line for a transportation of a substance and/or a signal transmission, in addition to the insertion head. For such a supply line and/or discharge line, a housing in accordance with the present invention advantageously forms a supporting section which, in particular, may be formed as a support. If the supply line and/or discharge line is releasably connected to the housing or the puncturing device, as may be preferred, the supporting section of the housing advantageously supports a connector to which the supply line and/or discharge line is connected. It is advantageous if the supporting section forms a guide for the connector which in the positioned state of the insertion head is parallel to the tissue surface, so that the connector in the direction of the tissue surface along the guide can be connected slidingly, fluidically and/or with respect to signalling technique to the housing or directly to the puncturing device. Mechanically, the connector is connected to the housing.

In some embodiments, in addition to a flexible element, the puncturing device comprises a stabilizing element, for example a puncturing needle, a handle part of the stabilizing element may be received in the supporting section when the puncturing device adopts its protected position. In such embodiments, the handle part of the stabilizing element and the connector use the same supporting section of the housing.

DETAILED DESCRIPTION

Figure 1:
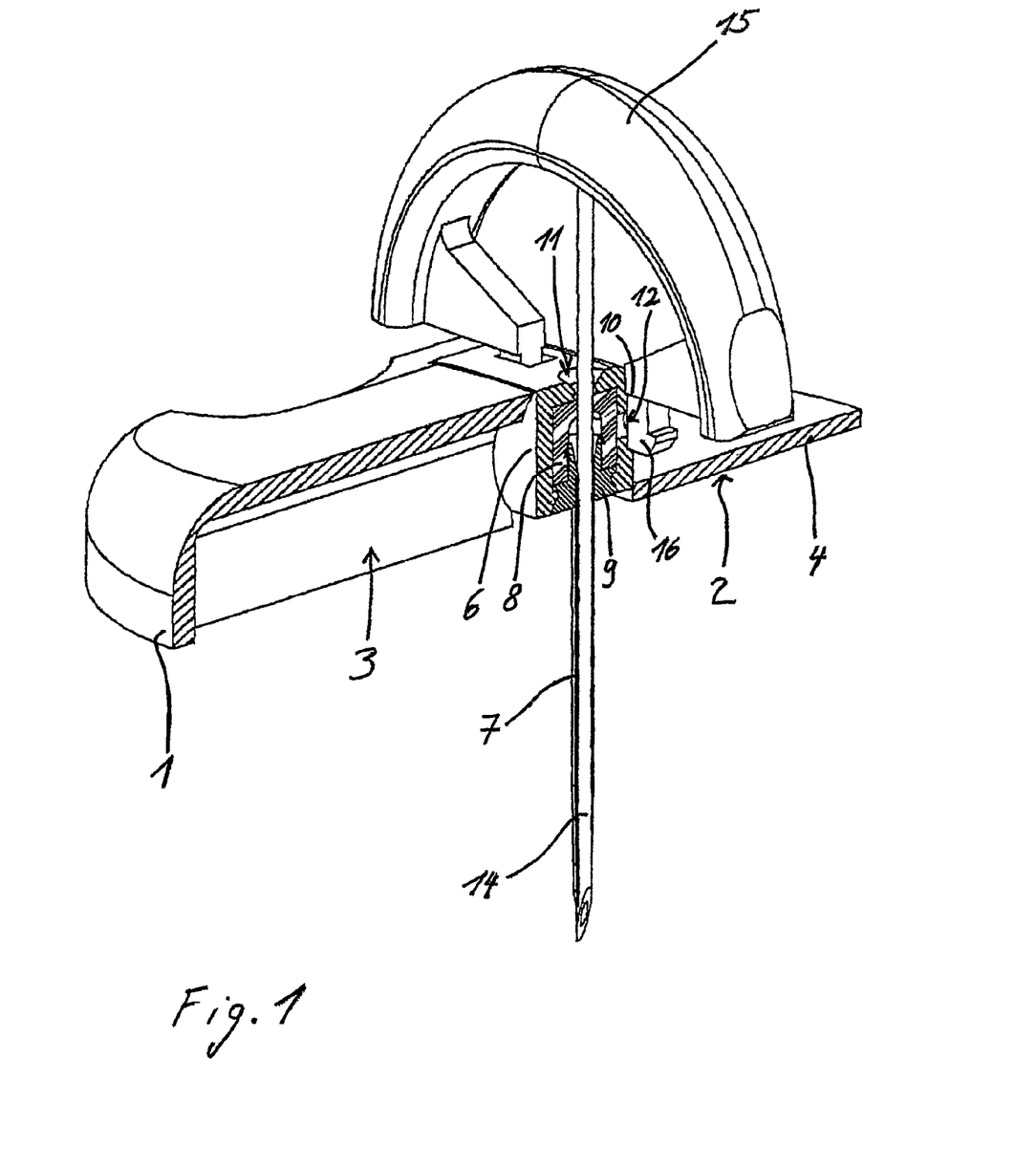
FIG. 1 depicts one embodiment of an insertion head in accordance with the present invention with a puncturing device in a puncturing position before the inserting into organic tissue.

FIG. 1 shows, in longitudinal section, an embodiment of an insertion head in accordance with the present invention. The insertion head comprises a housing 1 and a puncturing device or structure which is shown partially in a puncturing position relative to the housing 1. The puncturing device comprises a connecting structure or connector 6 which is permanently connected in a movable manner to the housing 1. The puncturing device further comprises a flexible penetrating element 7 which, in this embodiment, is formed as a cannula with an inner cross section of flow through which, when the insertion head 1 is used as an infusion head of an infusion set, a fluid infusate, for example insulin, flows. The penetrating element 7 is so flexible that, without an additional stabilization, it is not able to penetrate through the skin of a patient and is not able to penetrate into the skin. For the inserting of the penetrating element 7, a sufficiently rigid stabilizing element 14 in the form of a puncturing needle projects through the connecting structure 6 and the penetrating element 7 projecting therefrom, so that the stabilizing element 14 projects with a free tip beyond the free end of the flexible penetrating element 7. The flexible penetrating element 7 closely surrounds the peripheral outer surface of the stabilizing element 14 with a light tension.

The penetrating element 7 and the stabilizing element 14 form a puncturing section of the puncturing device which, in the puncturing position shown in FIG. 1, projects or extends at right angles beyond an underside 2 of the housing 1. For use, the insertion head 1 can be moved with the underside 2 generally facing the skin, wherein the stabilizing element 14 pierces the skin and the puncturing section penetrates into and through the skin until the underside 2 contacts the skin surface. The underside 2 may be formed as an adhesive surface which is covered with a pull-off film, which is pulled-off for use to expose the adhesive surface. As soon as the underside 2 contacts the skin surface, an adhesive connection is therefore automatically produced.

The stabilizing element 14 is provided with a handle part 15. The handle part 15 has the shape of one half of a ring. The stabilizing element 14 projects from a central area from the inner side of the handle part 15 and beyond the ring ends of the handle part 15. In the two outer end regions of the handle part 15 a connecting element 16 projects radially inwardly from the inner side thereof. The connecting element 16 serve for the fastening of the handle part 15 and, thus, jointly of the stabilizing element 14, to the connecting structure 6. The two connecting elements 16 of the handle part 15 each form a hook-shaped catching element, which releasably catches with a corresponding counter element in a recess of the connecting structure 6. The catching engagement of the two connecting elements 16 can be released by the two ring ends of the handle part 15 being pressed towards one another, counter to the restoring elasticity thereof, and the handle part is then moved away from the connecting structure 6. In this case, the stabilizing element 14 is pulled out of the flexible penetrating element 7 so that after the removal of the stabilizing element 14 only the penetrating element 7 still remains in the tissue.

The connecting structure 6 forms a hollow space which is open on one side, from which the penetrating element 7 projects, and further comprises a passageway 11 for the stabilizing element 14 opposite the open side and a second passageway 12 for the connection of an infusate supply line. In the hollow space a sealing element 8 is arranged which seals the two passageways 11 and 12. The flexible penetrating element 7 projects from a holder 9, which closes the hollow space of the connecting structure 6, apart from the cross section of flow of the penetrating element 7, on the open side thereof and is held there positively and non-positively on the connecting structure 6. At the same time, the holder 9 also holds the connecting element 8 within the hollow space of the connecting structure 6 so that, by pressing against the two passageways 11 and 12, it sealingly closes same. The sealing element 8 forms, together with the holder 9 in the hollow space, a chamber 10 through which, during an infusion, the infusate flows into the flexible penetrating element 7. The sealing element 8 is formed such that it may be pierced by the stabilizing element 14, and/or so that both in the pierced state and after the stabilizing element 14 is removed, seals the passageways 11 and 12.

The housing 1 comprises three sections. In a central section of the three sections, the housing 1 holds the connecting structure 6. To the one side of the central section, the housing 1 forms or defines a receptacle 3 in the form of a hollow space which opens toward the underside 2 of the housing 1 and toward the connecting structure 6. The connecting structure 6 is held by the housing 1 in such a manner that it is set back a small distance behind the underside 2. To the other side of the central section, the housing 1 forms a supporting section 4 in the form of a plate-shaped or disc-shaped flat part.

Figure 2:
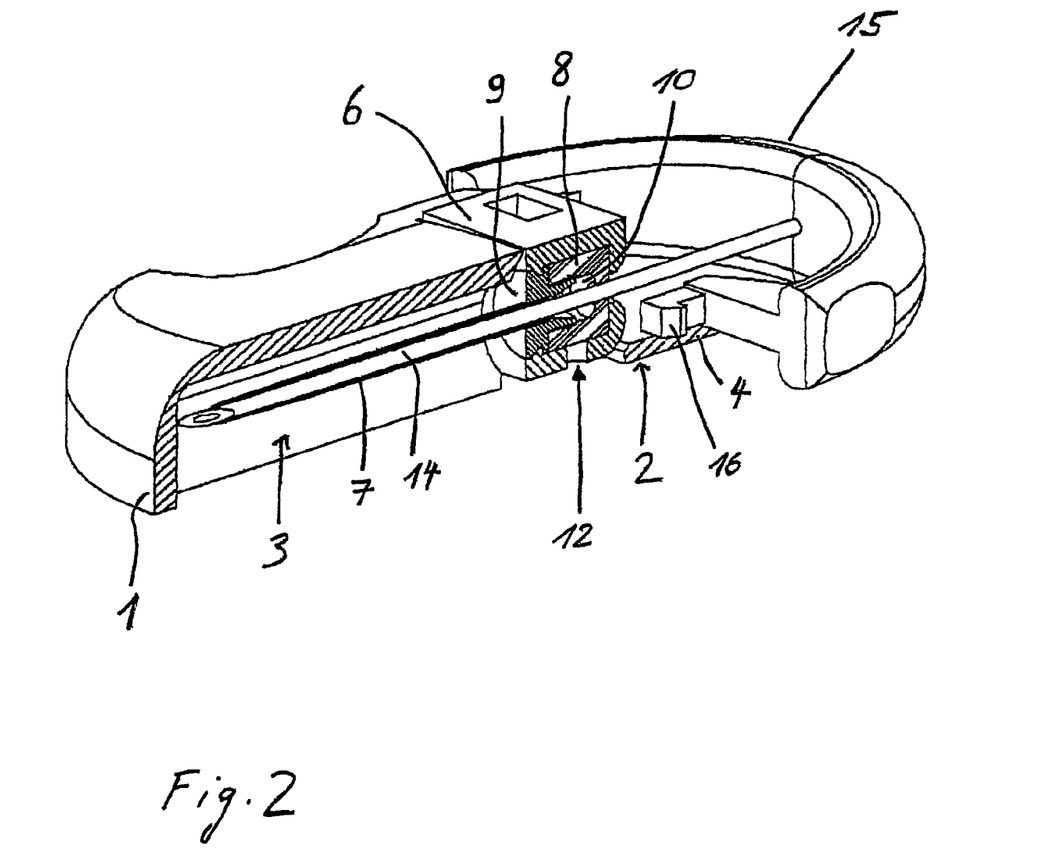
FIG. 2 shows the insertion head with the puncturing device in a protected position.

FIG. 2 shows the insertion head in the same sectional view as FIG. 1, wherein the puncturing device adopts or has been moved to a protected position, in which its entire puncturing section is received in the receptacle 3. The transfer from the puncturing position into the protected position takes place by a rotary movement of the connecting structure 6 about a rotational axis pointing or extending transversely to the puncturing section.

By the rotational movement of the connecting structure 6 the puncturing section may be pivoted into the hollow space 3. The handle part 15, which beyond the connecting structure 6 lies opposite the puncturing section 7, is used by the user not only as a handle for pulling out of the stabilizing element 14 but also as a pivoting handle. In the protected position of the puncturing device, the handle part 15 rests on the upper side of the supporting section 4, which thus forms a support for the handle part 15.

The insertion head is delivered to a point of use with the puncturing device located in its protected position. FIG. 2 thus shows the insertion head in the delivery state. In this state, the height of the insertion head is low, measured to the underside 2. The volume of the sterile packaging of the insertion head can be accordingly small. Generally, the length and width of an insertion head in accordance with the present invention can correspond to the corresponding dimensions of conventional insertion heads thus reducing the need for special handling or packaging. The minimum height is predetermined by the connecting structure 6, which is provided with the connections 11 and 12 for the stabilizing element 14 and an infusate supply line, with a connecting device for the connection to the housing 1 and with a connecting device for the handle part 15. The supporting section 4 and the handle part 15 pivoted thereon, together have approximately the height of the housing section provided with the receptacle 3.

Figure 3:
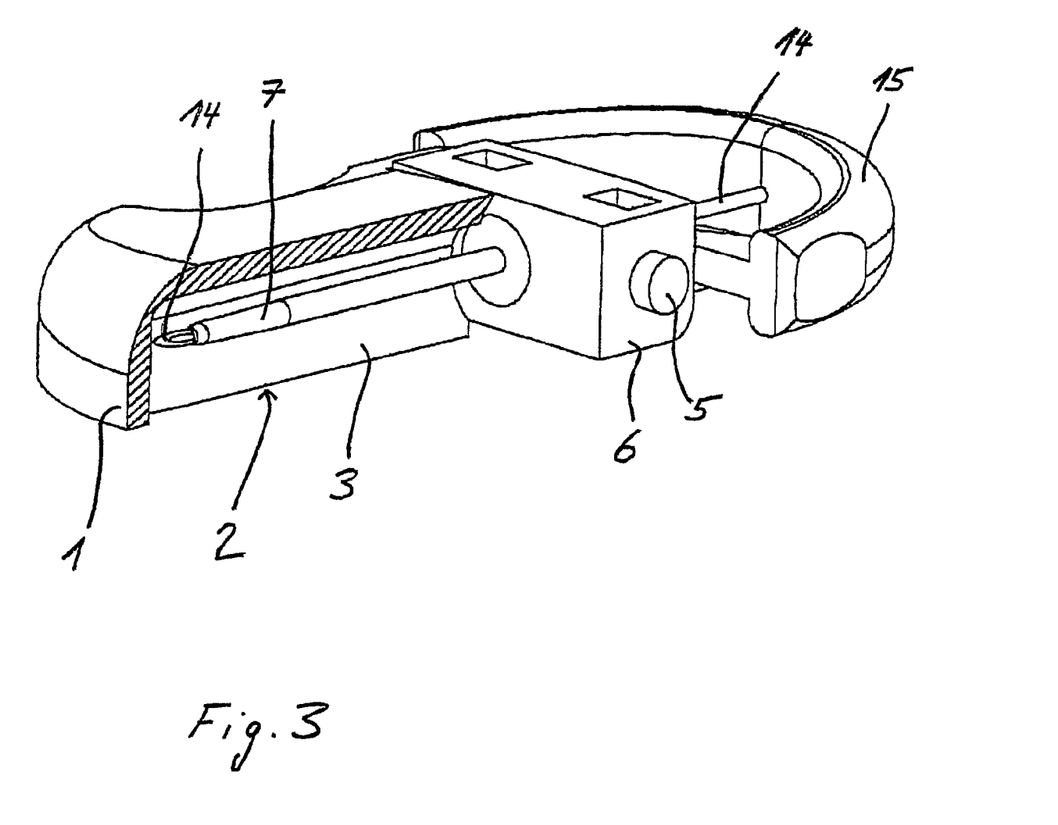
FIG. 3 shows the insertion head with the puncturing device shown in the protected position.

FIG. 3 shows the insertion head with the puncturing device located in the protected position or orientation thereof. While the housing section forming the hollow space 3 is shown again in longitudinal section of FIGS. 1 and 2, FIG. 3 shows the connecting structure 6 in a perspective view. The connecting structure 6 forms, on two sides opposing one another, one pivot pin 5. The two pivot pins 5 project transversely to the puncturing section. The housing 1 forms for each of the pivot pins 5 one articulated bushing. The connecting structure 6 and the housing 1, therefore, form in each case one articulated element of a simple swivel joint with a single axis of articulation, about which the connecting structure 6 rotatably, and the puncturing section thereby pivotably is connected to the housing 1. The connecting structure 6 may, therefore, also be denoted as a rotary head. The connection with the housing 1 is further designed such that the connecting structure 6 forms, both in the protected position and puncturing positions, a catching connection with the housing 1.

Figure 4:
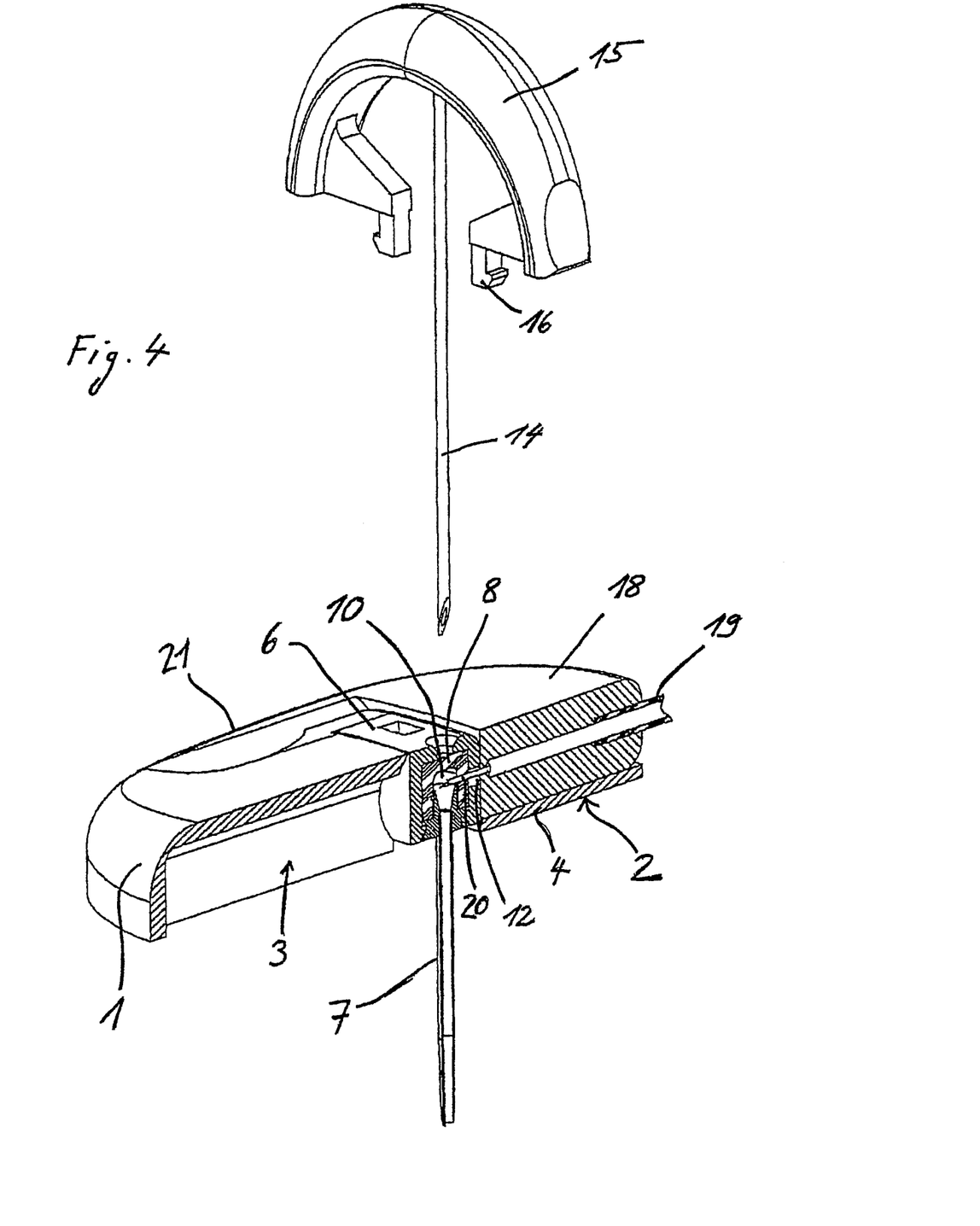
FIG. 4 shows the insertion head with the puncturing device in the puncturing position and a connected fluid supply line.

FIG. 4 shows the insertion head with an attached infusate supply line 19. The supply line 19 can be formed by a flexible catheter. The stabilizing element 14 is released from the connecting structure 6 and can, for example, be placed in the packaging of the insertion head.

The infusate supply line 19 is fixedly connected to a connector 18 which provides the connection of the infusate supply line 19 to the connecting structure 6 and thereby to the flexible penetrating element 7. The handle part 15 forms two connecting elements 16 for the mechanical fastening to the housing 1 of which one is shown in the longitudinal section of FIG. 4. Alternatively, the positive connection of the handle part 15, assuming appropriate modifications, could be formed with the connecting structure 6. The longitudinal section plane shown in FIG. 4 forms a plane of symmetry of the insertion head including the connector 18. The two connecting elements 16 are flexurally elastic and at their ends in each case are provided with one catching element in the form of a hook. The connector 18 further comprises an underside which is shaped to correspond to the upper side of the supporting section 4, so that the connector can be slidably pushed over the upper side of the supporting section 4 toward the connecting structure 6 until the connection to the puncturing device and a catching connection with the housing 1 are established. For the fluidic connection, the connector 18 forms a connecting needle 20 which, at least substantially parallel to the underside of the connector 18, protrudes therefrom in the pushing forward direction thereof. Upon pushing the connector 18 to the connecting structure 6, the needle penetrates the sealing element 8 thereof, so that the connecting needle 20 projects with its tip into the chamber 10. The connecting needle 20 is hollow and the connector 18 forms a cross-section of a line which connects the infusate supply line 19 to the connecting needle 20. In this manner, after the connection, a fluid-tight connection is established from the infusate supply line 19 up to the free end of the penetrating element 7.

An embodiment of a sequence or method of use of an insertion head in accordance with the present invention is as follows:

The insertion head reaches the user packaged in a sterile manner in the delivery state shown in FIG. 2. The user opens the packaging and removes the insertion head. Due to the integrated protective device formed by the housing 1 in the form of the receptacle 3 and the puncturing device located in the protected position thereof, the user is protected from puncturing injuries and the puncturing section is protected from damage.

In a next step, the pull-off film is removed from the underside 2 of the housing 1, so that the adhesive surface of the underside 2 is exposed. The user holds the housing 1 with one hand and grips the handle part 15 with the other hand. The handle part 15 may then be pivoted about the rotational axis formed by the swivel joint and, as a result, pivots the puncturing device into the puncturing position shown in FIG. 1, in which the puncturing section projects beyond the underside 2 of the housing. In this state, the user presses the insertion head against the skin, so that the puncturing section penetrates into and through the skin, until the insertion head contacts the skin surface and the underside 2 thereof and thereby adheres to the skin surface by adhesive forces. The free end of the flexible penetrating element 7 is automatically positioned in the tissue, e.g. subcutaneously, by puncturing. The stabilizing element 14 can now be removed by the user pressing together the two ring ends of the handle part 15, bringing the connecting elements 16 thereof out of engagement with the connecting structure 6, and pulling out the handle part 15 with the stabilizing element 14 fastened thereto of the connecting structure 6 and of the penetrating element 7. The sealing element 8 ensures that the cross section of flow of the penetrating element 7 is sealed in a sterile manner from the surroundings even after the pulling out.

The insertion head is now ready for the connection of the infusate supply line 19 (FIG. 4). For the connection, the connector 18, resting on the supporting section 4 of the housing 1, is pushed forward, with the connecting needle 20 ahead, onto the connecting structure 6. During this pushing movement, the connecting needle 20 penetrates through the passageway 12 and the sealing element 8 into the chamber 10. At the same time, the connecting elements 21 of the connector 18 come into catching engagement with the housing 1 so that, firstly, the fluidic connection and, secondly, the mechanical connection of the infusate supply line 19 to and with the flexible penetrating element 7 is established, as shown in FIG. 4.

If the pull-off film has a cut-out in the region of the receptacle 3, the pull-off film can also only be removed after pivoting away the puncturing section 7, 14.

After use, the connector 18 is released from the housing 1. The insertion head is released from the skin surface and the flexible penetrating element 7 is pulled out of the tissue.

Figure 5:
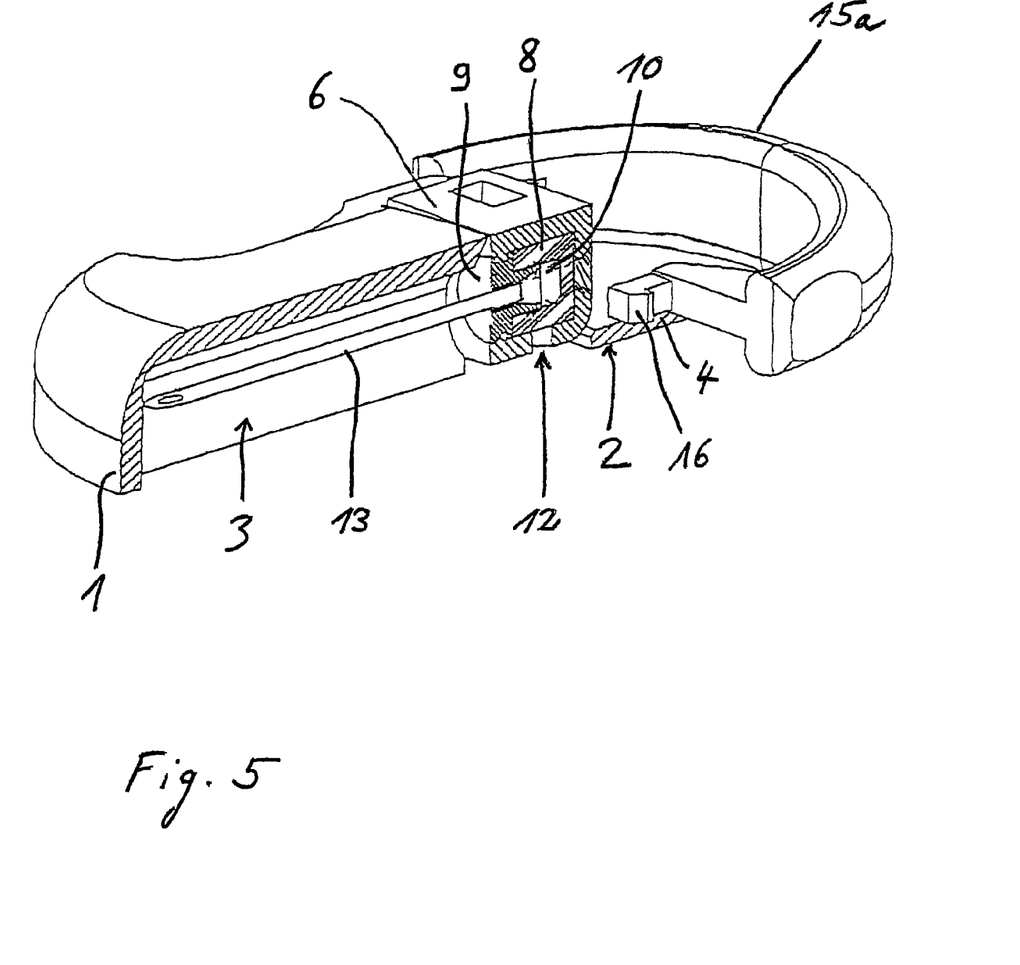
FIG. 5 depicts another embodiment of an insertion head in accordance with the present invention in longitudinal section.
Figure 6:
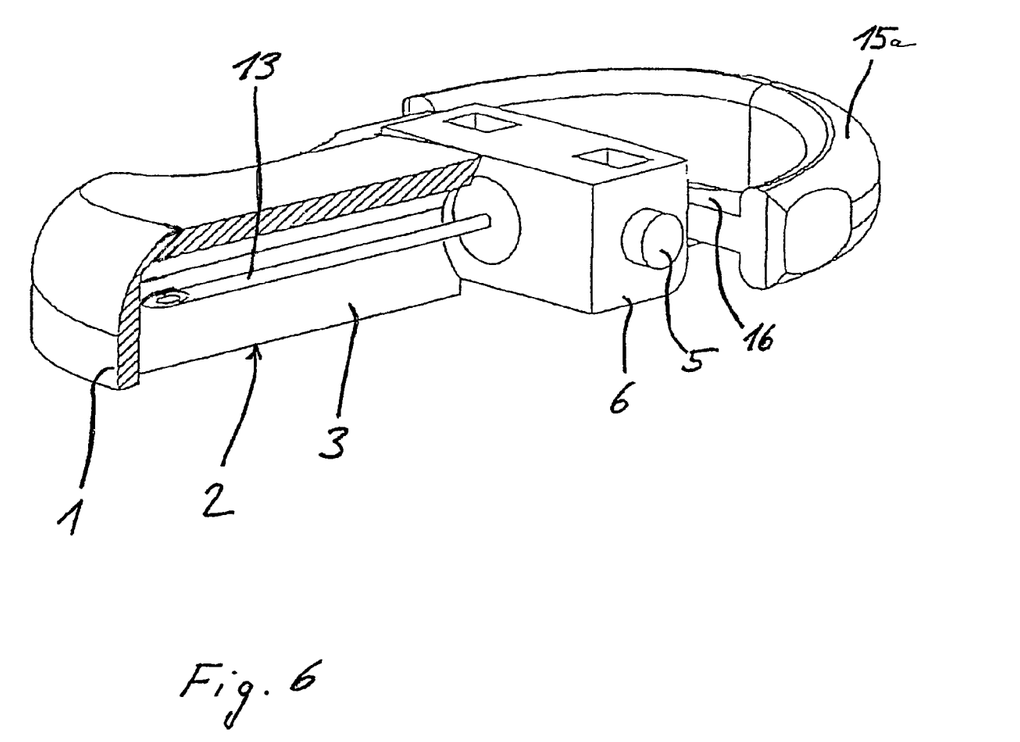
FIG. 6 is another view of the insertion head of the embodiment of FIG. 5.

FIGS. 5 and 6 show another embodiment of an insertion head in accordance with the present invention with a puncturing device located in the protected position in longitudinal section. The insertion head comprises a one-piece puncturing section 13, which during the use, e.g. the administration of a product, remains in the tissue. The stabilizing element 14 of the embodiment described with reference to FIGS. 1-4 is dispensed with. The puncturing section 13 may be formed as a conventional puncturing needle, e.g. a piercing cannula, for example as steel needle. Such a puncturing section 13 should be as flexible as possible to cause as little irritation as possible in the tissue. However, it has to have a minimum amount of flexural strength to be able to penetrate into and through the skin further into the tissue. In one development, the puncturing section 13 which remains in the tissue, which also may form a cutting element for penetrating into the tissue, at least partially consists of a material which, as a result of contact with tissue, becomes more flexible. Suitable materials include, but are not limited to polymers which bind at least one component of body fluid which the puncturing section 13 contacts in the tissue.

In some embodiments, the bindable component is water. As a result of the binding, the respective material becomes softer, but maintains its integrity to such an extent that the cross section of flow formed by the puncturing section 13 remains continuously open for the transportation of the product.

The insertion head of the exemplary embodiment of FIGS. 5 and 6 comprises a handle 15*a* which is modified relative to the embodiment described with reference to FIGS. 1-4. The slope of handle 15*a* corresponds to the handle 15 of the first embodiment, but is no longer connected to a stabilizing element, but formed only as a handle part 15*a*. The handle 15*a* serves for the transfer of the puncturing device into the puncturing position, and as the case may be, also for the return from the puncturing position into the protected position. The handle 15*a* may further be used, as is the case with the handle 15 of the first embodiment, as the handle for the entire insertion head, to position the head on a tissue, e.g. human skin.

The handle 15a may further also serve as a handle when releasing the insertion head from the tissue. During use, the handle 15a is released from the remainder of the insertion head. For release from the tissue surface the handle 15a can again be caught to the connecting structure 6 and can be used as a handling aid for the release. The handle 15a may also be used as an additional part for releasing the insertion head.

The insertion head of the embodiment shown in FIGS. 5 and 6 generally corresponds to the embodiment of FIGS. 1-4, but for the sake of completeness it should be appreciated that the connecting structure 6 naturally does not have to have a passageway for the stabilizing element 14, due to the omission of the stabilizing element 14. The passageway 11 is accordingly dispensed with, but could in principle, with corresponding sealing, remain in the connecting structure 6.

The fluid chamber 10 could, in the second embodiment, be converted into a simple cross section of flow which continuously lengthens the puncturing section 13 up to the passageway 12 and in which a sealing disc is provided to seal the passageway or the connection 12, respectively, from the surroundings.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An insertion head for medical or pharmaceutical applications, the insertion head comprising:
    a) a housing with an underside which can be positioned on organic tissue and a support surface facing away from the underside; and
    b) a puncturing device comprising a puncturing section with a tip and a handle, the puncturing device movably held by the housing such that the puncturing device moves from an initial, protected position in which the housing covers the tip and the puncturing section is substantially parallel to the organic tissue, to a puncturing position in which the tip projects beyond the underside,
    wherein the puncturing section comprises a flexible penetrating element and a stabilizing element for the penetrating element, in the puncturing position the puncturing section is tilted relative to its position in the protected position, in the puncturing position the distal end of the flexible penetrating element is oriented in the same direction as the distal end of the stabilizing element, and the handle rests on the support surface when the puncturing device is in the protected position.

2. The insertion head according to claim 1, wherein the puncturing device is permanently connected to the housing such that it is movable from the protected position to the puncturing position.

3. The insertion head according to claim 1, wherein the puncturing section is connected to the housing in a swiveling manner.

4. The insertion head according to claim 1, wherein the puncturing device and the housing form with one another an articulation with an axis of articulation about which the puncturing device is rotatable relative to the housing.

5. The insertion head according to claim 4, wherein the axis of articulation is generally transverse to the puncturing section.

6. The insertion head according to claim 1, wherein the housing also holds the puncturing device in a predetermined further puncturing position, wherein the puncturing section in one of the puncturing positions has an inclination with respect to the bottom side which is different from that in the other puncturing position.

7. The insertion head according to claim 1, wherein the housing holds the puncturing device either positively and/or non-positively in a catching connection in at least one of the positions.

8. The insertion head according to claim 1, wherein the housing comprises a receptacle which, in the protected position, receives at least the tip of the puncturing section.

9. The insertion head according to claim 8, wherein the receptacle is open toward an outer side of the housing.

10. The insertion head according to claim 9, wherein the receptacle is open toward the underside.

11. The insertion head according to claim 8, wherein the puncturing device comprises a connecting structure connected to the housing in an articulated manner and from which the puncturing section projects, and in that the receptacle opens toward the connecting structure.

12. The insertion head according to one claim 1, wherein the puncturing section comprises or is a line element for a fluid.

13. The insertion head according to claim 12, wherein the puncturing device comprises a fluid chamber with a fluid connection connected to the line element and a seal for the fluid connection.

14. The insertion head according to claim 1, wherein the puncturing device comprises a connecting structure connected to the housing, the puncturing section projecting from the connecting structure.

15. The insertion head according to claim 14, wherein the connecting structure has a connection for a fluid or signals.

16. The insertion head according to claim 14, wherein the housing and the connecting structure form with one another an articulation by which the puncturing device is movably connected to the housing between catching positions in which the connecting structure and the housing catch.

17. The insertion head according to claim 14, wherein the handle projects from the connecting structure and is releasably connected thereto.

18. The insertion head according to claim 14, wherein the stabilizing element is releasably connected to the connecting structure.

19. The insertion head according to claim 18, wherein the handle holds the stabilizing element at a proximal end.

20. The insertion head according to claim 19, wherein the stabilizing element is attached to the connecting structure by a catching connection.

21. The insertion head according to claim 1, wherein the puncturing section comprises a puncturing needle, which remains in the tissue during the application.

22. The insertion head according to claim 1, wherein the puncturing section is or comprises a puncturing needle which remains in the tissue during the application, and wherein the flexibility of the puncturing needle increases upon contact with the tissue.

23. The insertion head according to claim 22, wherein the puncturing needle consists at least partially of a polymer material which binds at least one component of a body fluid, and wherein the flexibility of the puncturing needle increases as a result of the binding.

24. The insertion head according to claim 1, wherein the handle projects from the housing for handling the insertion head when placing the insertion head on the tissue or removing the insertion head from the tissue.

25. The insertion head according to claim 1, further comprising a connector having a line element for a fluid or signals which can be attached to the puncturing device.

26. The insertion head according to claim 25, wherein the connector is mechanically connected to the housing.

27. The insertion head according to claim 26, wherein the handle holds the stabilizing element at a proximal end and the support surface forms a guide for the connector when the connector is connected to the puncturing device.

28. The insertion head according to claim 1, wherein the puncturing section is movable relative to the underside of the housing into an angular position between 0 and 90° below the housing.

29. An insertion head comprising:
a) a housing comprising an underside, wherein a receptacle of the housing in the form of a hollow space opens toward the underside;
b) a penetrating structure with a tip, wherein the penetrating structure is held by a connecting structure of the housing and comprises a removable stabilizing element; and
c) at least one pivot pin on the connecting structure matching an articulated bushing formed by the housing to form a simple swivel joint, wherein the connecting structure holding the penetrating structure can pivot about the pivot pin to cause movement of the penetrating structure from an initial, protected orientation in which the tip of the penetrating structure is located within the receptacle and is arranged substantially parallel to the housing underside, to a penetrating orientation in which the tip of the penetrating structure protrudes below the receptacle and is angled relative to its position in the protected orientation.

30. The insertion head according to claim 29, further comprising a handle connected to the stabilizing element.

31. An insertion head comprising:
a) a housing comprising an underside, wherein a receptacle of the housing in the form of a hollow space opens toward the underside;
b) a penetrating structure with a tip, wherein the penetrating structure is held by a connecting structure of the housing;
c) at least one pivot pin on the connecting structure matching an articulated bushing formed by the housing to form a simple swivel joint, wherein the connecting structure holding the penetrating structure can pivot about the pivot pin to cause movement of the penetrating structure from an initial, protected orientation in which the tip of the penetrating structure is located within the receptacle and is arranged substantially parallel to the housing underside, to a penetrating orientation in which the tip of the penetrating structure protrudes below the receptacle and is angled relative to its position in the protected orientation; and
d) a handle comprising at least one hook-shaped catching element which releasably catches with a corresponding counter element in a recess of the connecting structure.

* * * * *